(12) United States Patent
Toure

(10) Patent No.: US 11,672,623 B2
(45) Date of Patent: Jun. 13, 2023

(54) SEPARABLE STERILE DRAPE WITH Z-SHAPED FOLDS

(71) Applicant: Creative Surgical Solutions, LLC, Edwards, CO (US)

(72) Inventor: Samba Toure, Grand Blanc, MI (US)

(73) Assignee: Creative Surgical Solutions, LLC, Vail, CO (US)

( * ) Notice: Subject to any disclaimer, the term of this patent is extended or adjusted under 35 U.S.C. 154(b) by 0 days.

(21) Appl. No.: 17/535,384

(22) Filed: Nov. 24, 2021

(65) Prior Publication Data

US 2022/0079699 A1 Mar. 17, 2022

Related U.S. Application Data

(62) Division of application No. 16/119,205, filed on Aug. 31, 2018, now Pat. No. 11,185,382.

(60) Provisional application No. 62/552,865, filed on Aug. 31, 2017.

(51) Int. Cl.
*A61B 46/20* (2016.01)
*A61B 46/00* (2016.01)
*A61B 90/00* (2016.01)
*A61B 17/00* (2006.01)

(52) U.S. Cl.
CPC .............. *A61B 46/20* (2016.02); *A61B 46/00* (2016.02); *A61B 46/40* (2016.02); *A61B 2017/00902* (2013.01); *A61B 2090/037* (2016.02)

(58) Field of Classification Search
CPC ......... A61B 46/00; A61B 46/20; A61B 46/40; A61B 2090/037; A61B 2017/00902
See application file for complete search history.

(56) References Cited

U.S. PATENT DOCUMENTS

| 2,353,858 A | 7/1944 | Tedesco |
| RE24,613 E | 3/1959 | Hageltorn |
| 2,960,561 A | 11/1960 | Plummer |
| 3,060,932 A | 10/1962 | Pereny et al. |

(Continued)

FOREIGN PATENT DOCUMENTS

| CN | 1214625 | 4/1999 |
| CN | 101721255 | 6/2010 |

(Continued)

OTHER PUBLICATIONS

File History of U.S. Appl. No. 61/352,045, filed Jun. 7, 2010.

(Continued)

*Primary Examiner* — Camtu T Nguyen
(74) *Attorney, Agent, or Firm* — Sheridan Ross P.C.

(57) ABSTRACT

An improved draping system with a drape and a lock device. The drape includes an area defined by a predetermined length and a predetermined width, as well as a selectively separable portion. The drape also has a first perforation, as well as a z-shaped fold over the perforation. The lock device may be a poly seal with a second perforation. The draping system is secured to an operating table to maintain sterility about that operating table. When ready for removal, the draping system is simply pulled in opposite directions. When this occurs, the second perforation breaks, which disengages the lock device. Upon further pulling, the z-shaped fold is unfolded. Further pulling still results in the second perforation breaking.

15 Claims, 14 Drawing Sheets

(56) References Cited

U.S. PATENT DOCUMENTS

| | | | |
|---|---|---|---|
| 3,255,809 | A | 6/1966 | Kawczynski |
| 3,682,163 | A | 8/1972 | Plummer |
| 3,698,395 | A | 10/1972 | Hansson |
| 3,741,203 | A | 6/1973 | Liman |
| 3,835,851 | A | 9/1974 | Villari |
| 3,882,859 | A | 5/1975 | Ericson |
| 4,090,508 | A | 5/1978 | Gaylord, Jr. |
| 4,153,054 | A | 5/1979 | Boone |
| 4,369,356 | A | 1/1983 | Tsurutani et al. |
| 4,627,426 | A | 12/1986 | Wegener et al. |
| 4,782,502 | A | 11/1988 | Schulz |
| 4,873,997 | A | 10/1989 | Marshall |
| 4,887,339 | A | 12/1989 | Bellanger |
| 4,905,710 | A | 3/1990 | Jones |
| 4,939,819 | A | 7/1990 | Moyer |
| 5,127,423 | A | 7/1992 | Draeger |
| 5,187,813 | A * | 2/1993 | Klein ............... A41D 13/08 2/16 |
| 5,263,970 | A | 11/1993 | Preller |
| 5,503,163 | A | 4/1996 | Boyd |
| 5,515,868 | A | 5/1996 | Mills |
| 5,527,312 | A | 6/1996 | Ray |
| 5,569,246 | A | 10/1996 | Ojima et al. |
| 5,605,534 | A | 2/1997 | Hutchison |
| 5,651,375 | A | 7/1997 | Cunningham |
| 5,674,189 | A * | 10/1997 | McDowell ............ A61F 13/10 604/304 |
| 5,810,750 | A | 9/1998 | Buser |
| 5,817,038 | A | 10/1998 | Orange et al. |
| 5,865,846 | A | 2/1999 | Bryan et al. |
| 6,030,401 | A | 2/2000 | Marino |
| 6,113,602 | A | 9/2000 | Sand |
| 6,142,998 | A | 11/2000 | Smith et al. |
| 6,286,511 | B1 | 9/2001 | Levitt et al. |
| 6,290,724 | B1 | 9/2001 | Marino |
| 6,309,395 | B1 | 10/2001 | Smith et al. |
| 6,314,959 | B1 | 11/2001 | Griesbach et al. |
| 6,328,738 | B1 | 12/2001 | Suddaby |
| 6,364,880 | B1 | 4/2002 | Michelson |
| 6,719,795 | B1 | 4/2004 | Cornwall et al. |
| 7,014,640 | B2 | 3/2006 | Kemppanien et al. |
| 7,025,769 | B1 | 4/2006 | Ferree |
| 7,077,864 | B2 | 7/2006 | Byrd, III et al. |
| 7,182,088 | B2 | 2/2007 | Jenkins |
| 7,207,992 | B2 | 4/2007 | Ritland |
| 7,288,093 | B2 | 10/2007 | Michelson |
| 7,341,590 | B2 | 3/2008 | Ferree |
| 7,387,643 | B2 | 6/2008 | Michelson |
| 7,406,775 | B2 | 8/2008 | Funk et al. |
| 8,726,907 | B2 * | 5/2014 | Strauch ............. A61B 46/40 128/849 |
| 10,363,108 | B2 * | 7/2019 | Strauch ............. A61B 46/10 |
| 10,363,110 | B2 * | 7/2019 | Strauch ............. A61B 46/40 |
| 10,610,321 | B2 | 4/2020 | Ueda |
| 11,185,381 | B2 | 11/2021 | Srauch et al. |
| 11,185,382 | B2 | 11/2021 | Toure |
| 2006/0064797 | A1 | 3/2006 | Rowe et al. |
| 2006/0137693 | A1 | 6/2006 | Lewis et al. |
| 2007/0102005 | A1 | 5/2007 | Bonutti |
| 2007/0162096 | A1 | 7/2007 | Zakuto et al. |
| 2008/0000006 | A1 | 1/2008 | Ochoa et al. |
| 2008/0168995 | A1 | 7/2008 | Yardan et al. |
| 2008/0255564 | A1 | 10/2008 | Michelson |
| 2009/0277460 | A1 | 11/2009 | Carrez et al. |
| 2010/0031966 | A1 | 2/2010 | Allen |
| 2010/0186754 | A1 | 7/2010 | Carrez et al. |
| 2010/0192960 | A1 | 8/2010 | Rotolo |
| 2012/0312308 | A1 | 12/2012 | Allen |
| 2013/0072839 | A1 | 3/2013 | Cuypers et al. |
| 2014/0081291 | A1 | 3/2014 | Groke et al. |
| 2015/0114404 | A1 | 4/2015 | Czop et al. |
| 2021/0015576 | A1 | 1/2021 | Strauch et al. |
| 2022/0079698 | A1 | 3/2022 | Strauch et al. |

FOREIGN PATENT DOCUMENTS

| | | |
|---|---|---|
| FR | 2896146 | 7/2007 |
| WO | WO 2017/040454 | 3/2017 |

OTHER PUBLICATIONS

File History of U.S. Appl. No. 61/357,637, filed Jun. 23, 2010.
International Search Report for International Patent Application No. PCT/US2012/039555, dated Sep. 14, 2012, 3 pages.
Written Opinion for International Patent Application No. PCT/US2012/039555, dated Sep. 14, 2012, 4 pages.
International Preliminary Report on Patentability for International (PCT) Patent Application No. PCT/US2012/039555, dated Apr. 10, 2014 6 pages.
Official Action (with English Translation) for China Patent Application No. 2012800255508, dated Nov. 30, 2015 19 pages.
Notice of Allowance (with English translation) for China Patent Application No. 201280025550.8, dated Nov. 18, 2016 9, 5 pages.
Extended Search Report for European Patent Application No. 12789811.2, dated May 11, 2015 6 pages.
Article 94(3) Communication for European Patent Application No. 12789811.2, dated Oct. 8, 2019, 6 pages.
Official Action (no English translation available) for Mexican Patent Application No. MX/a/2019/011486, dated Jul. 23, 2020, 3 pages.
International Search Report and Written Opinion for International (PCT) Patent Application No. PCT/US16/49358, dated Nov. 10, 2016, 8 pages.
International Preliminary Report on Patentability for International (PCT) Patent Application No. PCT/US2016/049358, dated Mar. 15, 2018, 7 pages.
Extended European Search Report for European Patent Application No. 18191933.3, dated Jan. 17, 2019, 8 pages.
Official Action for U.S. Appl. No. 13/155,219 dated Nov. 21, 2012, 9 pages.
Official Action for U.S. Appl. No. 13/155,219, dated May 17, 2013 9 pages.
Official Action for U.S. Appl. No. 13/155,219, dated Sep. 13, 2013 12 pages.
Notice of Allowance for U.S. Appl. No. 13/155,219, dated Mar. 28, 2014 9 pages.
Official Action for U.S. Appl. No. 14/280,416, dated Oct. 26, 2016, 20 pages.
Official Action for U.S. Appl. No. 14/280,416, dated Mar. 14, 2017, 20 pages.
Official Action for U.S. Appl. No. 14/280,416, dated Jul. 12, 2017, 16 pages.
Official Action for U.S. Appl. No. 14/280,416, dated Mar. 22, 2018, 17 pages.
Official Action for U.S. Appl. No. 14/280,416, dated Dec. 13, 2018, 18 pages.
Notice of Allowance for U.S. Appl. No. 14/280,416, dated Mar. 6, 2019, 10 pages.
Official Action for U.S. Appl. No. 14/846,388, dated Oct. 4, 2016, 20 pages.
Official Action for U.S. Appl. No. 14/846,388 dated Feb. 8, 2018, 14 pages.
Official Action for U.S. Appl. No. 14/846,388 dated Mar. 30, 2018, 15 pages.
Official Action for U.S. Appl. No. 14/846,388 dated Sep. 24, 2018, 16 pages.
Notice of Allowance for U.S. Appl. No. 14/846,388 dated Mar. 15, 2019, 9 pages.
Official Action for U.S. Appl. No. 16/435,495, dated Aug. 28, 2020, 8 pages. Restriction Requirement.
Official Action for U.S. Appl. No. 16/435,495, dated Feb. 3, 2021, 12 pages.
Official Action for U.S. Appl. No. 16/119,205, dated Dec. 2, 2020, 11 pages.
Notice of Allowance for U.S. Appl. No. 16/119,205, dated Jun. 10, 2021, 10 pages.

(56) References Cited

OTHER PUBLICATIONS

Article 94(3) Communication for European Patent Application No. 12789811.2, dated Apr. 9, 2021, 6 pages.
Intention to Grant for European Patent Application No. 12789811.2, dated Nov. 3, 2021 42 pages.
International Search Report and Written Opinion for International (PCT) Patent Application No. PCT/US2021/053345, dated Jan. 27, 2022 13 pages.
Notice of Allowance for U.S. Appl. No. 16/435,495, dated Jun. 30, 2021, 8 pages.
Official Action for U.S. Appl. No. 17/535,347, dated Jan. 6, 2023 12 pages.

* cited by examiner

SEPARABLE STERILE DRAPE WITH Z-SHAPED FOLDS

CROSS-REFERENCE TO RELATED APPLICATIONS

This application is a divisional of U.S. patent application Ser. No. 16/119,205, filed Aug. 31, 2018, which claims the benefit of priority of U.S. Provisional Patent Application Ser. No. 62/552,865, filed on Aug. 31, 2017 and titled Separable Sterile Drape with Z-Shaped Folds, the entire contents of both of which are hereby expressly incorporated by reference into the present application.

BACKGROUND OF THE INVENTION

1. Field of the Invention

The present invention relates in general to the field of medical procedures. More particularly, the present invention relates to drapes used during medical procedures to improve sterile conditions. Specifically, a preferred embodiment of the present invention relates to a drape that maintains sterility beneath the drape before two different portions of the drape are separated from one another.

2. Discussion of the Related Art

It is important during any surgical procedure to maintain sterility about an operating room. Compromises in sterility can result in contaminations, which present significant health concerns to patients and significant costs to the hospital or medical facility. This is especially true with surgeries related to the spinal cord and associated nerves. To prevent contamination of an open surgical wound, surgical staff often isolate the operative site from the surrounding nonsterile environment. This can be accomplished by creating and maintaining the sterile field and by following aseptic principles aimed at preventing microorganisms from contaminating the surgical wound.

One way to achieve this goal is by using a variety of different sterile drape products. Some of these drapes rest on top of various parts of the operating room prior to, and during medical procedures. For instance, drapes can be placed onto a patient, operating room furniture, or on top of various medical equipment by scrubbed personnel. These drapes establish an aseptic barrier minimizing the passage of microorganisms from nonsterile to sterile areas. Additionally, during certain surgical procedures these drapes must be removed in the middle of surgery where temporary sterile coverage is required. This removal results in an increased risk of sterility breaches.

U.S. Pat. No. 8,726,907 and Application Publication Nos. 2014/0251346 and 2015/0374442, all of which are incorporated herein by reference in their entirety, have introduced a number of different drapes used throughout the medical field to help avoid potential breaches in sterility. The drapes shown in this patent and applications feature various separable elements to help facilitate easy removal of the drape during medical procedures. While providing many advantages over prior art drapes, these drapes can still be improved upon. For instance, during some medical procedures, the air within an operating room is removed by a vacuum a number of times. Additionally, the room may be refilled with another gas, such as ethylene oxide, to kill bugs or other contaminates. Due to the repeated evacuation of air from the operating room, the drape may break into the separable elements inadvertently.

What is needed therefore is a drape system that can be placed about an operating room on a patient, a piece of furniture, or various medical equipment to maintain sterility about the operating room, while also providing a way for the drape to be easily removed. What is further needed is a drape system with separable elements to allow the drape to be easily removed without risking that the drape breaks apart before intended.

SUMMARY AND OBJECTS OF THE INVENTION

By way of summary, the present invention is directed to a draping system, a method of using the draping system, and a method of manufacturing a draping system.

A primary object of the invention is to provide an apparatus that helps to maintain sterility about an operating room. In accordance with a first aspect of the invention, these objects are achieved by providing an apparatus comprising a drape and a lock device. The drape may include an area that is defined by a predetermined length and a predetermined width. The drape may also include a selectively separable portion extending along a longitudinal portion of the drape. Additionally, the drape may have a first peripheral edge at a first terminus of the predetermined width and a second peripheral edge at a second terminus of the predetermined width. The first and second peripheral edges are adapted to at least partially overlap one another to form a z-shaped fold. Additionally, a plurality of handles may be attached to the area.

The lock device is configured to maintain the first and second peripheral edges in the z-shaped fold until the lock device is disengaged. For instance, the lock device could be a poly seal with a perforation extending therethrough. Alternatively, the lock device could be a piece of adhesive tape. Alternatively still, the lock device could be a plurality of hook and loop fasteners. Similarly, the lock device could be a plurality of clamps.

In accordance with another aspect of the invention, a method of using the drape system is provided. First, a drape system is placed on a sterile surface. The drape system may include a drape and a lock device as described above. Next, the drape system is unfolded about the sterile surface. Thereafter, the lock device may be disengaged. Additionally, opposite ends of the drape can be pulled away from one another, the z-shaped fold can be unfolded, the drape can be broken about the perforation, and the sterility beneath the drape can be maintained. Additional steps may include grasping at least two handles attached to opposite sides of the drape and then pulling the handles in opposite directions. This can cause the z-shaped fold to be unfolded and the drape to be broken about the perforation while also maintaining sterility beneath the drape. Additionally, a plurality of straps may be wrapped around the sterile surface. Next, ends associated with the plurality of straps may be affixed to the area to secure the drape to the sterile surface. Finally, a piece of medical equipment may be moved adjacent to the sterile surface.

In accordance with another aspect of the invention, a method of manufacturing a draping system is provided. First, a sheet is manufactured with a predetermined length and a predetermined width. Next, a perforation is formed substantially midway between the predetermined width along the entire length of the sheet. After the perforation is formed, the sheet may be folded such that a first peripheral edge overlaps over a second peripheral edge. For instance, the first peripheral edge and the second peripheral edge may form a three-inch overlap. When this occurs, the perforation is located between the first peripheral edge and the second peripheral edge. Additionally, a portion of the sheet covers the perforation when the sheet is folded. Also, a lock device may be secured to the sheet such that the sheet remains in the folded configuration until the lock device is disengaged.

The method of manufacturing may have additional steps. For instance, a poly seal may be heat sealed to the sheet. Alternatively, at least one piece of tape may be applied to the sheet. Alternatively still, a plurality of hook and loop fasteners may be applied to the sheet and the complementary hook and loop fasteners may be engaged with one another. Also, directional labels may be installed onto the sheet. Additionally, handles may be installed to the sheet. Also, the sheet may be folded into a compact shape while maintaining sterility about the sheet.

These, and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

Figure 1:
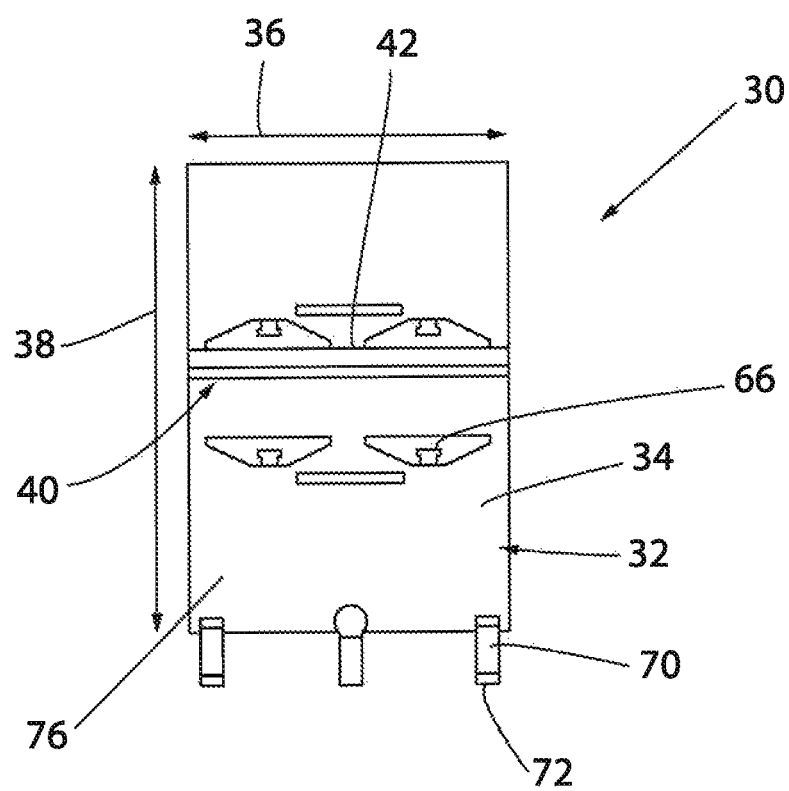
FIG. 1 illustrates a top plan view of a draping system with a drape and a lock device according to the present invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected, attached, or terms similar thereto are often used. They are not limited to direct connection but include connection through other elements where such connection is recognized as being equivalent by those skilled in the art.

DESCRIPTION OF PREFERRED EMBODIMENTS

The present invention and the various features and advantageous details thereof are explained more fully with reference to the non-limiting embodiments described in detail in the following description.

1. System Overview

As discussed above, the z-fold taught by U.S. Pat. No. 8,726,907 and Application Publication Nos. 2014/0251346 and 2015/0374442 is an essential feature to a drape used during medical procedures. It helps to better maintain sterility during and after surgical procedures, such as during spinal surgery when using a 3-dimensional radiographic device, as well as increasing efficiency of the surgical procedure. However, the drape can be further improved. When the drape is unfolded, the amount of force applied to the drape can vary depending on the individuals located on either side of the drape. As a result, where excessive force is used, the z-fold can inadvertently get disengaged during the unfolding process before the drape is fully installed. When this occurs, the drape is rendered useless and must be replaced by a new drape. Additionally, stickers used to engage the various portions of the drape can break, tear, or stick together before or during the draping process, which can compromise sterility. Obviously, this results in a waste of time, money, and resources associated with the disposal of the drape.

Further still, during certain medical procedures, the air within the operating room is repeatedly evacuated to ensure sterility about the room. When this occurs, the z-fold can be disengaged, or the various layers of the z-fold can stick together. Traditionally, the sticking issues could be addressed by including a blocking additive. However, the inclusion of additives can reduce the transparency of the drape, which is problematic during procedures using navigation systems that require sensors to see through the drape.

To address these issues, the current invention relates to a drape that includes a lock device that is used with the z-fold. By having a lock device, such as a strip of poly that is sealed across the z-fold like a bridge, the z-fold is contained under the bridge, and is therefore protected by the bridge. The strip of poly seal can also have a perforation line in the middle. Thus, to separate the drape, the perforation line in the strip of poly seal must first be broken. Once this has been broken, the z-fold is exposed and can be separated, after which time the drape can be separated about the perforation found in the z-fold. This allows the patient drape to be removed in a sterile manner. Of course, the lock device could have a number of other configurations, including pieces of adhesive tape, hook-and-loop fasteners, clamps, and the like.

2. Detailed Description of Preferred Embodiments

The inventive draping system 30 is generally shown in the figures. The draping system 30 includes a drape 32 with a z-shaped fold 52 and a lock device 54. The lock device 54 provides additional protection against inadvertent disengagement of the z-shaped fold 52 as will further be described below.

The drape 32 may include any of the features described in U.S. Pat. No. 8,726,907 and Application Publication Nos. 2014/0251346 and 2015/0374442. For instance, the drape 32 may include an area 34 with a predetermined length 36 and a predetermined width 38 as shown in FIG. 1, where the length 36 and the width 38 are of sufficient size to encompass a patient 82 on an operating table 84, along with any tools or instruments needed to perform a surgical procedure.

Figure 2:
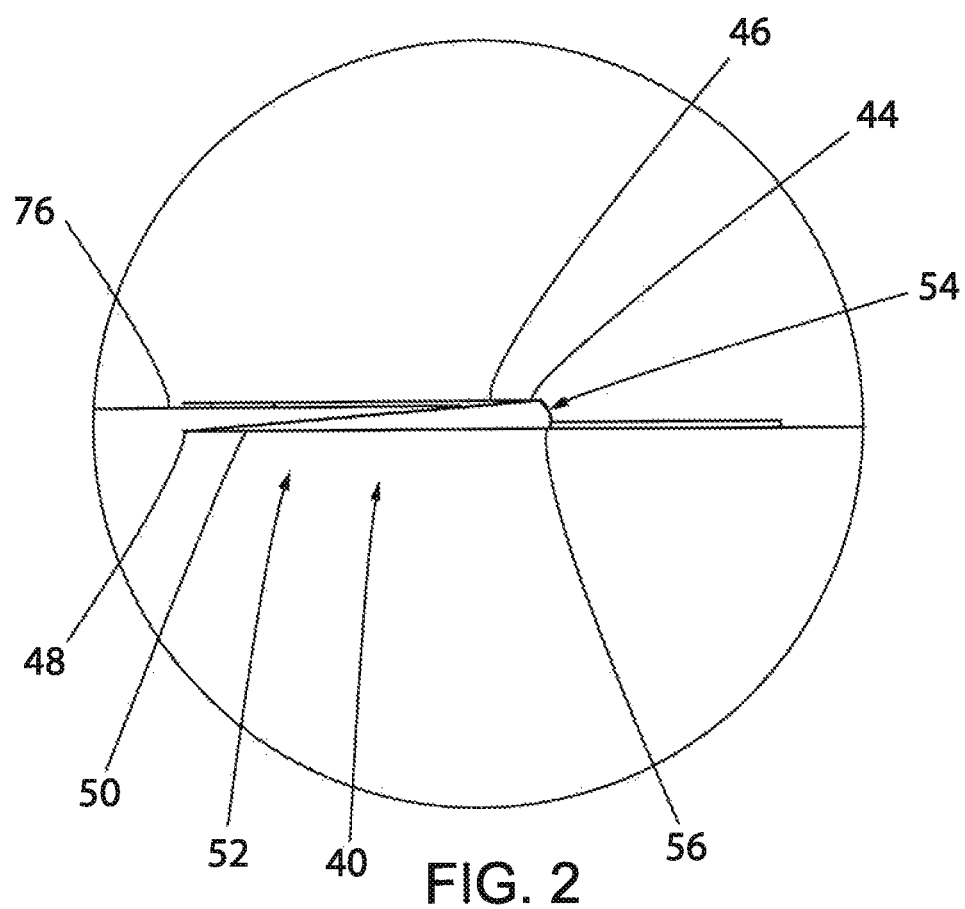
FIG. 2 illustrates a detailed view of the lock device and a z-shaped fold of the draping system of FIG. 1.
Figure 3:
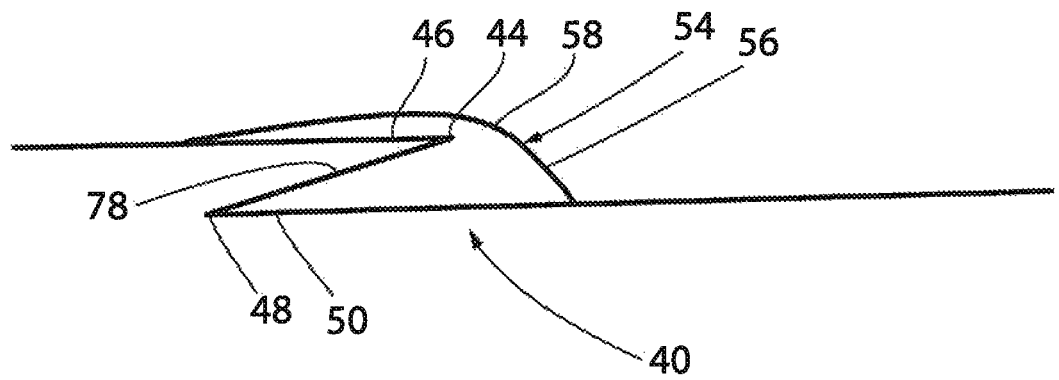
FIG. 3 illustrates another detailed side view of the draping system of FIG. 1 where lock device is shown to be pulled away to more easily see a drape of the drape.

Additionally, the drape 32 may feature a selectively separable portion 40 that extends along a longitudinal portion 42 of the drape 32 as can be seen in FIGS. 2 and 3. More specifically, the drape 32 also includes a first peripheral edge 44 at a first terminus 46 and a second peripheral edge 48 at a second terminus 50 of the predetermined width 38. The first peripheral edge 44 overlaps the second peripheral edge 48 to form the z-shaped fold 52 at the selectively separable portion 40. The drape 32 may also have a perforation 78 that extends between the first peripheral edge 44 and the second peripheral edge 48 and overlies the sterile field. For instance, the perforation 78 could be located at the second peripheral edge 48. Alternatively, the perforation 78 could be offset from the second peripheral edge 48. The perforation 78 allows for the drape 32 to easily be separated about the perforation 78. While the perforation 78 may or may not be visible to the naked eye, it has been identified as a dashed line in the figures. The perforation 78 allows the drape 32 to become detached by pulling or tearing the drape 32 in opposite directions parallel to the perforation 78. This causes the z shaped fold 52 to unfold. Once the z-shaped 52 is fully unfolded, the perforation 78 can break. Thereafter, the two opposing halves of the drape 32 may fall on either side of the sterile field without compromising sterility. As a result, the drape 32 can initially remain secured to provide a sterile field and also be sterilely separated about the selectively separable portion 40. Of course, the drape 32 could include features other than a perforation that allow the drape 32 to easily be separated.

The drape 32 may also include a plurality securing straps 70 attached to the area 34 that are wrapped around the patient 82 and the operating table 84. The securing straps 70 may have a fastener 86 located on an end 72 of the straps 70. For instance, the fastener 86 could be adhesives, pins, clips, snaps, hook-and-loop fasteners, clamps, magnetic strips, or any other fastener as known to one of ordinary skill in the art. Once the fasteners 86 are engaged, the drape 32 is secured about the operating table 84. Of course, the drape 32 need not include the straps 70 but could instead be secured to itself about the operating table 84.

Additionally, the draping system 30 may include a plurality of handles 66. For instance, as shown the handles 66 are attached to the drape 32 on either side of the first peripheral edge 44 and the second peripheral edge 48. These handles 66 help to facilitate the separation of the drape 32 about the selectively separable portion 40. Although the handles 66 are shown as separate components that are attached to the drape 32, it should also be noted that the handles 66 could be formed with the drape 32.

As shown in FIGS. 11-13, 17, 21, 23, 24, and 25, the lock device 54 comprises a poly seal 56 that extends across the middle of the drape 32. More specifically, the lock device 54 extends from beyond the first peripheral edge 44 and the second peripheral edge 48. The poly seal 56 may also have a perforation 58 that extends along the longitudinal portion 42 of the drape 32. Like the perforation 78 described above, the perforation 58 may or may not be visible by the naked eye but has been shown in the figures as a dashed line. Due to the lock device 54, before the first peripheral edge 44 and the second peripheral edge 48 can be separated to unfold the z-shaped fold 52, the poly seal 56 must first be broken about the perforation 58. Like the drape 32, to disengage the lock device 54, the draping system 30 is pulled in two opposite directions parallel to the perforation 58. Alternatively, the lock device 54 could take a number of other forms, including at least one piece of adhesive tape, at least one set of hook and loop fasteners, at least one clamp, or the like. These lock devices 54 can be disengaged, after which the draping system 30 can be pulled in opposite directions.

Next, a method of manufacturing the draping system 30 will be described. Initially, a sheet 76 is manufactured with a predetermined length 36 and a predetermined width 38.

Thereafter, a perforation 78 is formed in the sheet 76 midway between the predetermined width 38 along the entire length of the sheet 76. As stated above, the perforation 78 could be located at the second peripheral edge 48 or it could be slightly offset from the second peripheral edge 48. Once the perforation 78 has been formed, the sheet 76 is folded such that the first peripheral edge 44 overlaps over the second peripheral edge 48. For instance, there could be an approximately 3-inch overlap. As this occurs, the perforation 78 is located between the first peripheral edge 44 and the second peripheral edge 48. Additionally, when this occurs a portion of the sheet 76 covers the perforation 78. Next, the lock device 54 is secured to the sheet 76 such that the sheet 76 remains in the folded configuration until the lock device 54 is disengaged. For instance, a poly seal 56 having a perforation 58 formed therein may be heat sealed to the sheet 76 to form the lock 54. Alternatively, adhesive tape could be applied, or hook and loop fasteners could be applied to form the lock. Next, the draping system 30 can be folded into a compact shape while also maintaining sterility about the sheet 76.

Figure 4:
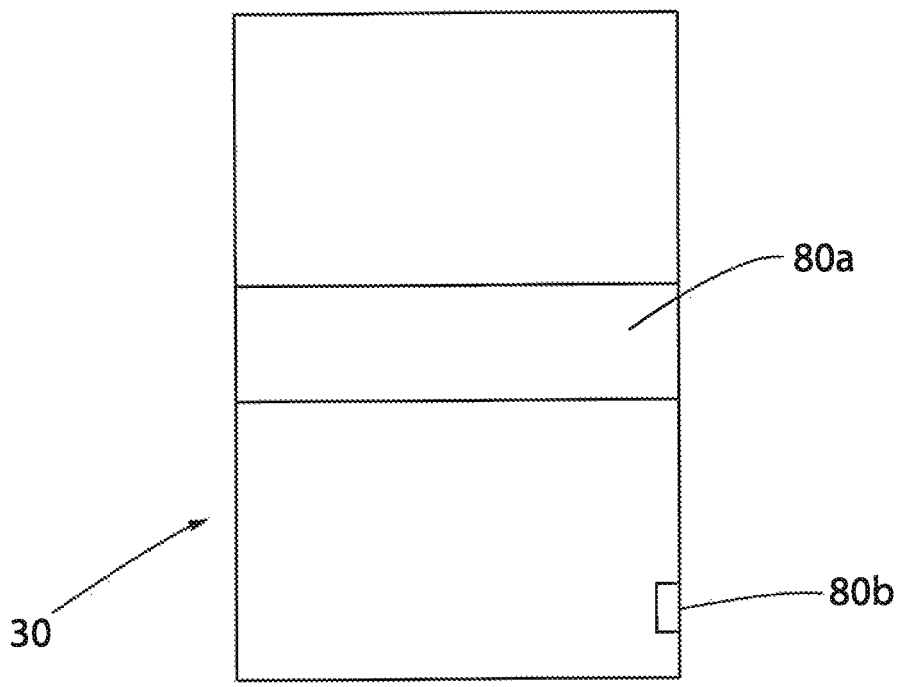
FIG. 4 illustrates a perspective view of the draping system in an initial folded configuration.
Figure 5:
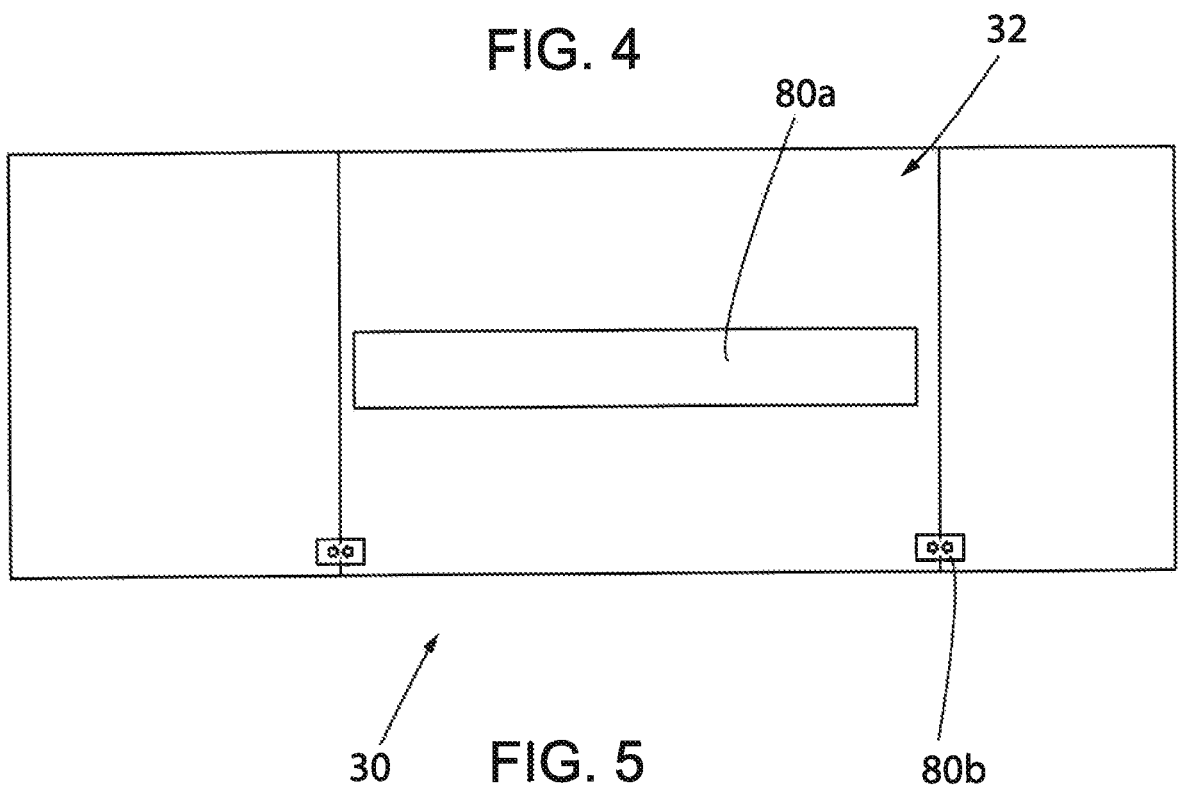
FIG. 5 illustrates a perspective view of the draping system of FIG. 5 in a partially unfolded configuration.
Figure 6:
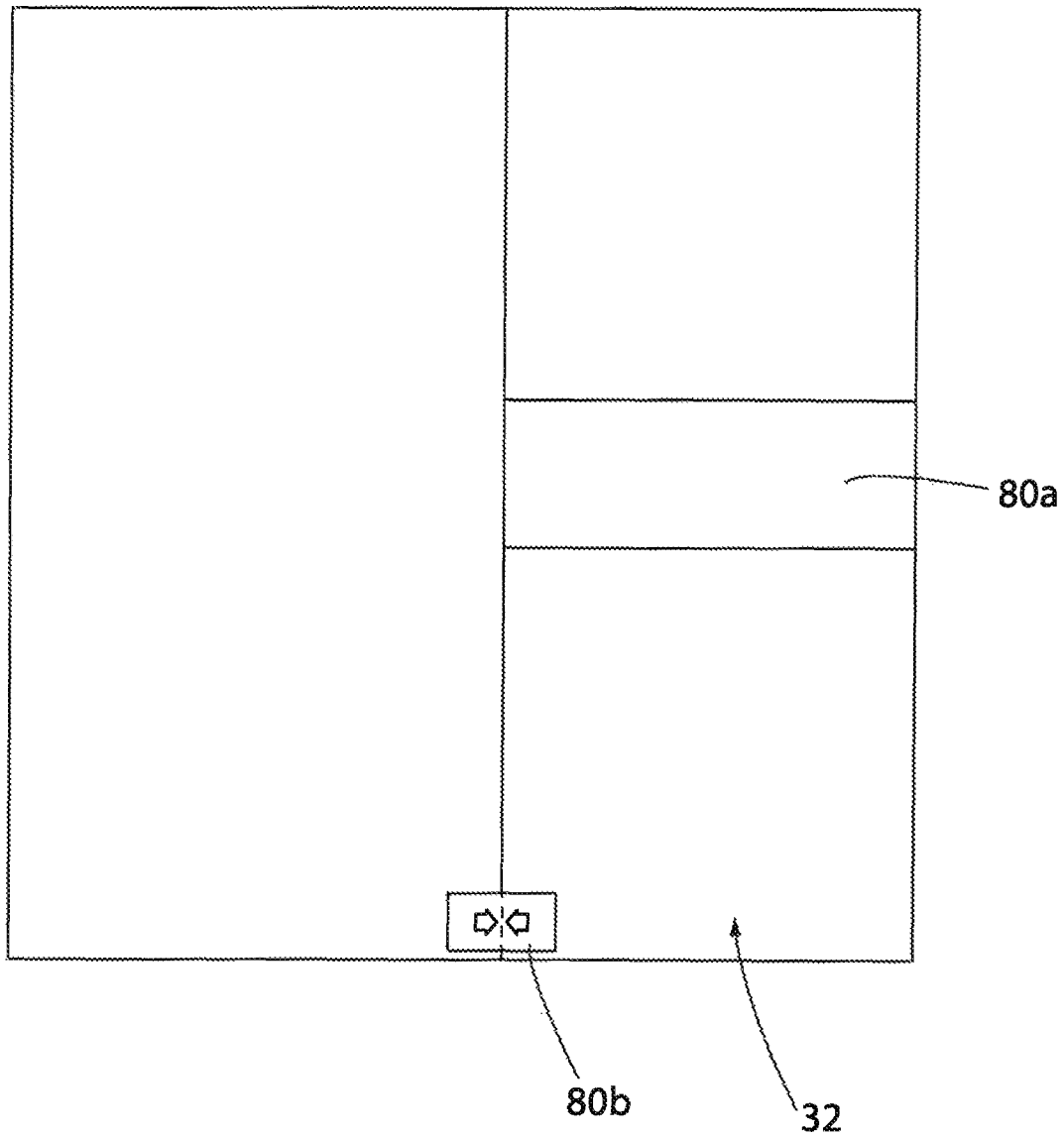
FIG. 6 illustrates a detailed view of a portion of the draping system of FIG. 5.
Figure 7:
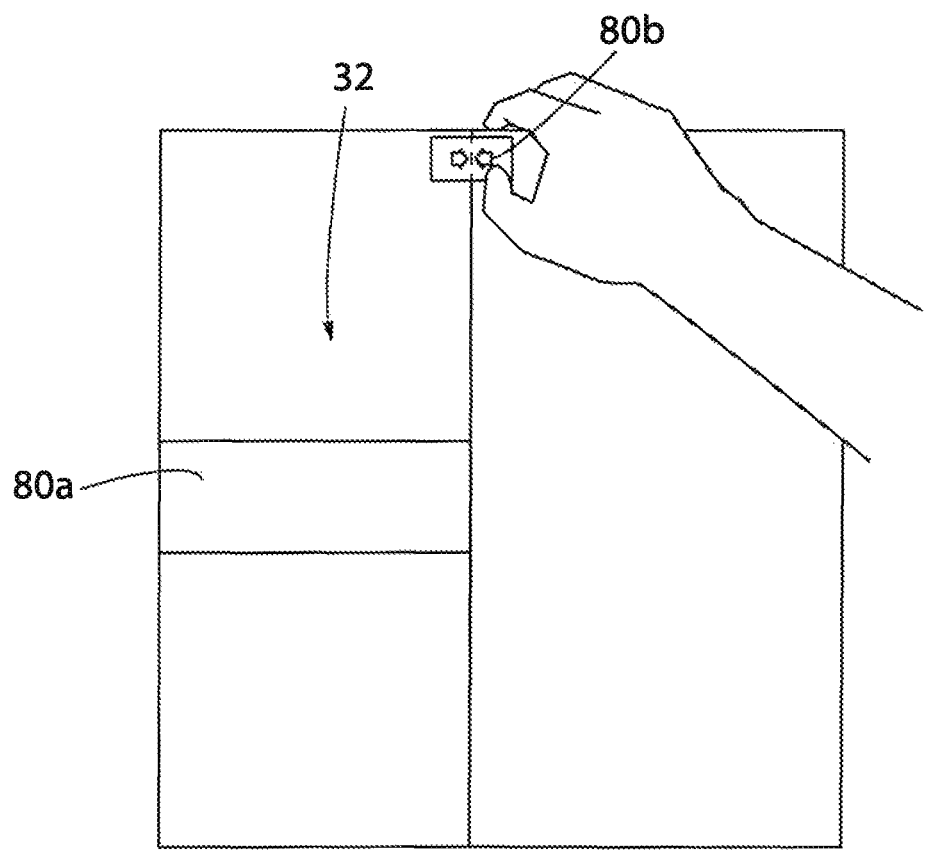
FIG. 7 illustrates a perspective view of the draping system of FIGS. 4-6 where a fastener is disengaged.
Figure 8:
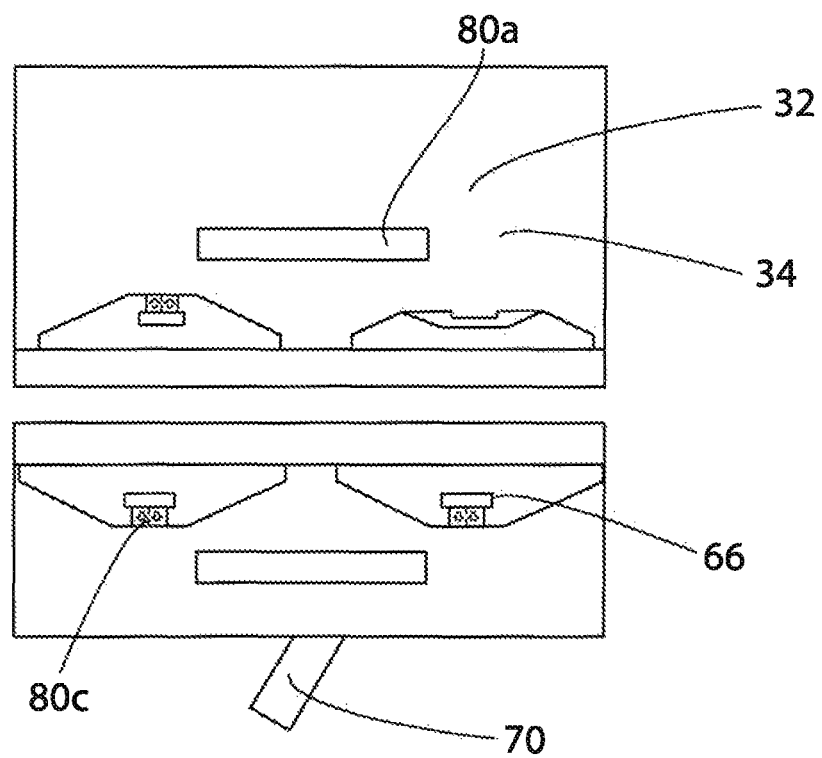
FIG. 8 illustrates a perspective view of the draping system of FIGS. 4-7 where the draping system is unfolded.
Figure 9:
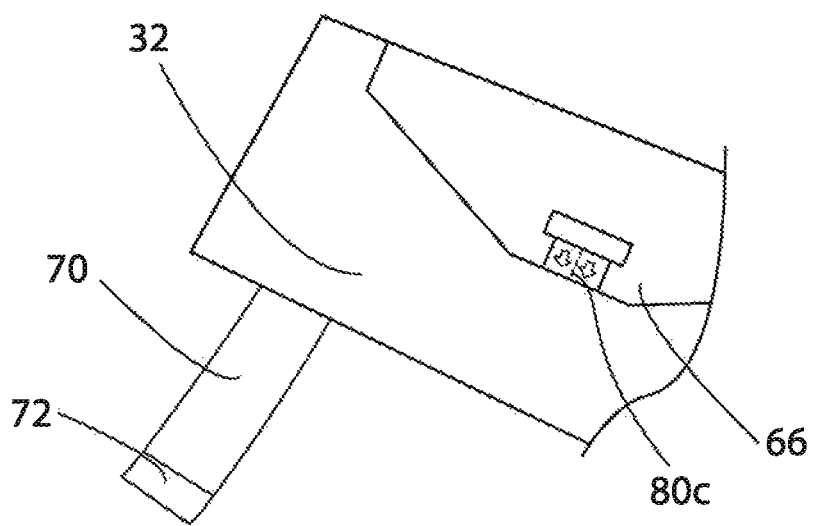
FIG. 9 illustrates a perspective view of the draping system of FIGS. 4-8 including a plurality of straps to secure the draping system about a sterile surface.
Figure 10:
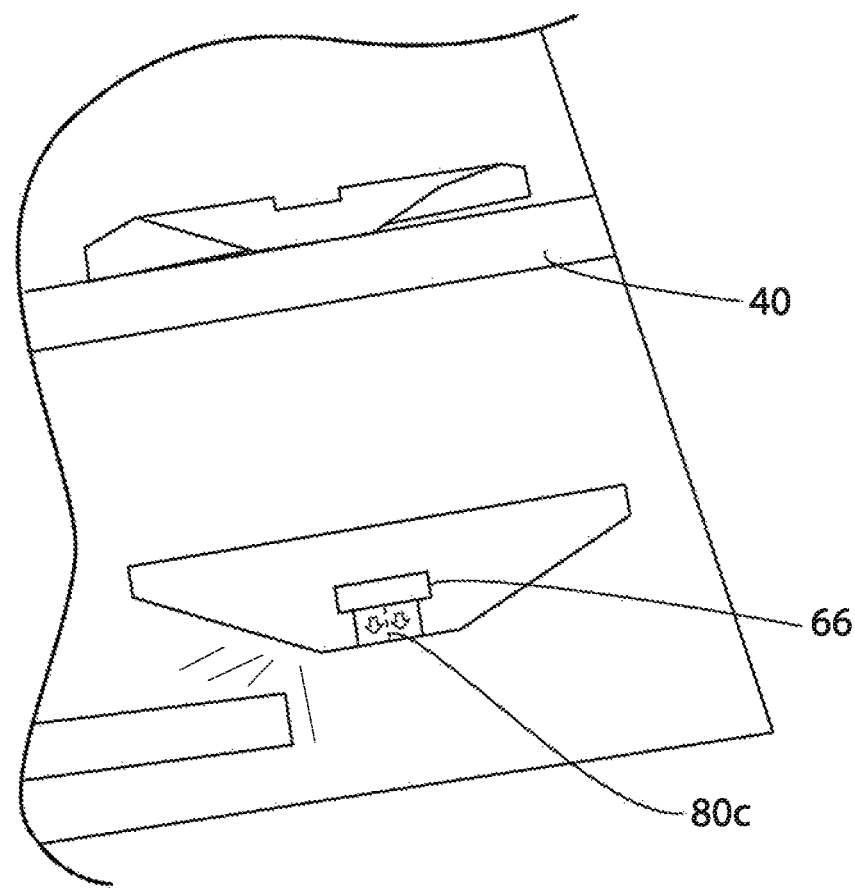
FIG. 10 illustrates a perspective view of the draping system of FIGS. 4-9 including a plurality of handles.
Figure 11:
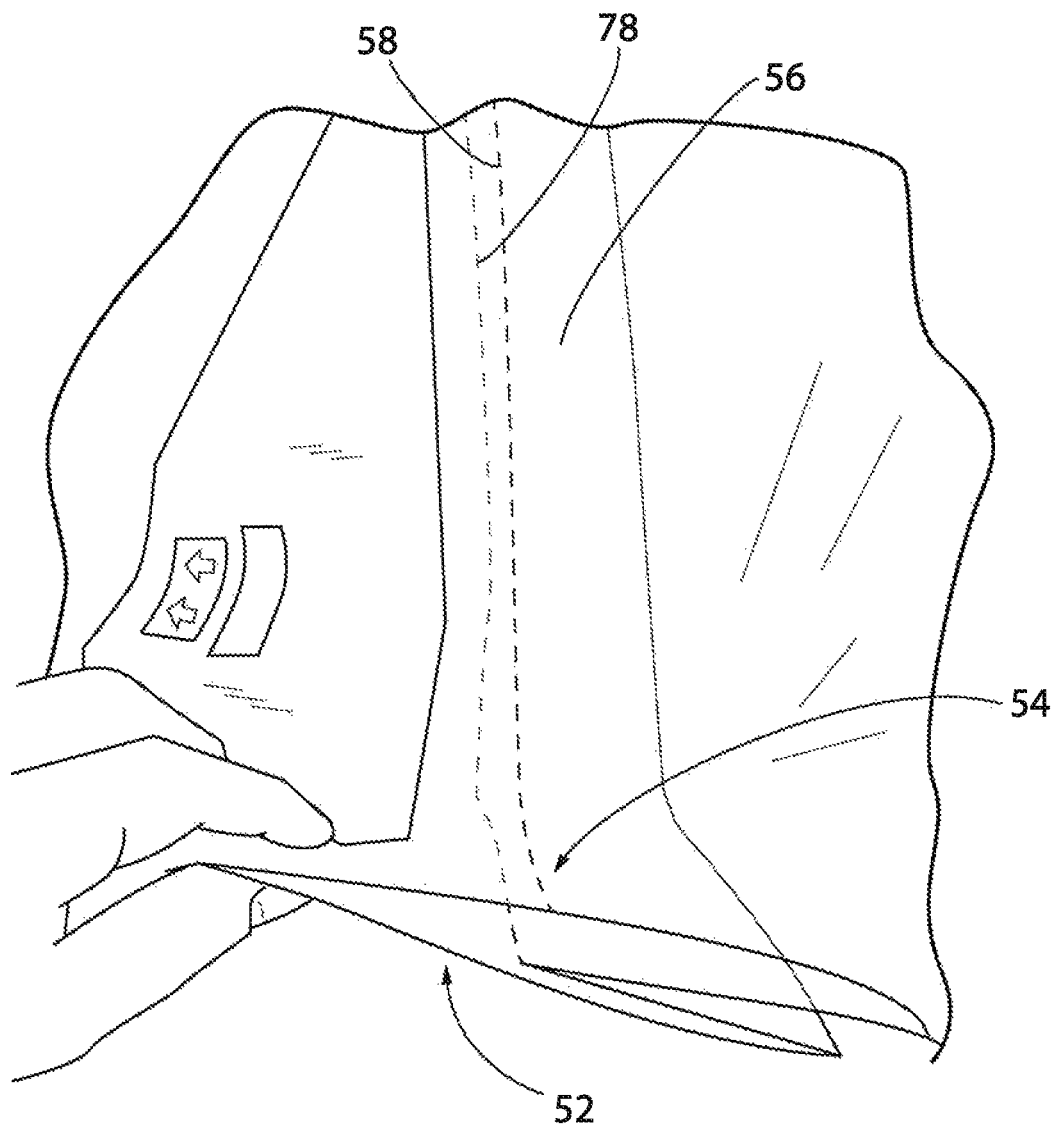
FIG. 11 illustrates a detailed perspective view of the z-fold the draping system of FIGS. 4-10.
Figure 12:
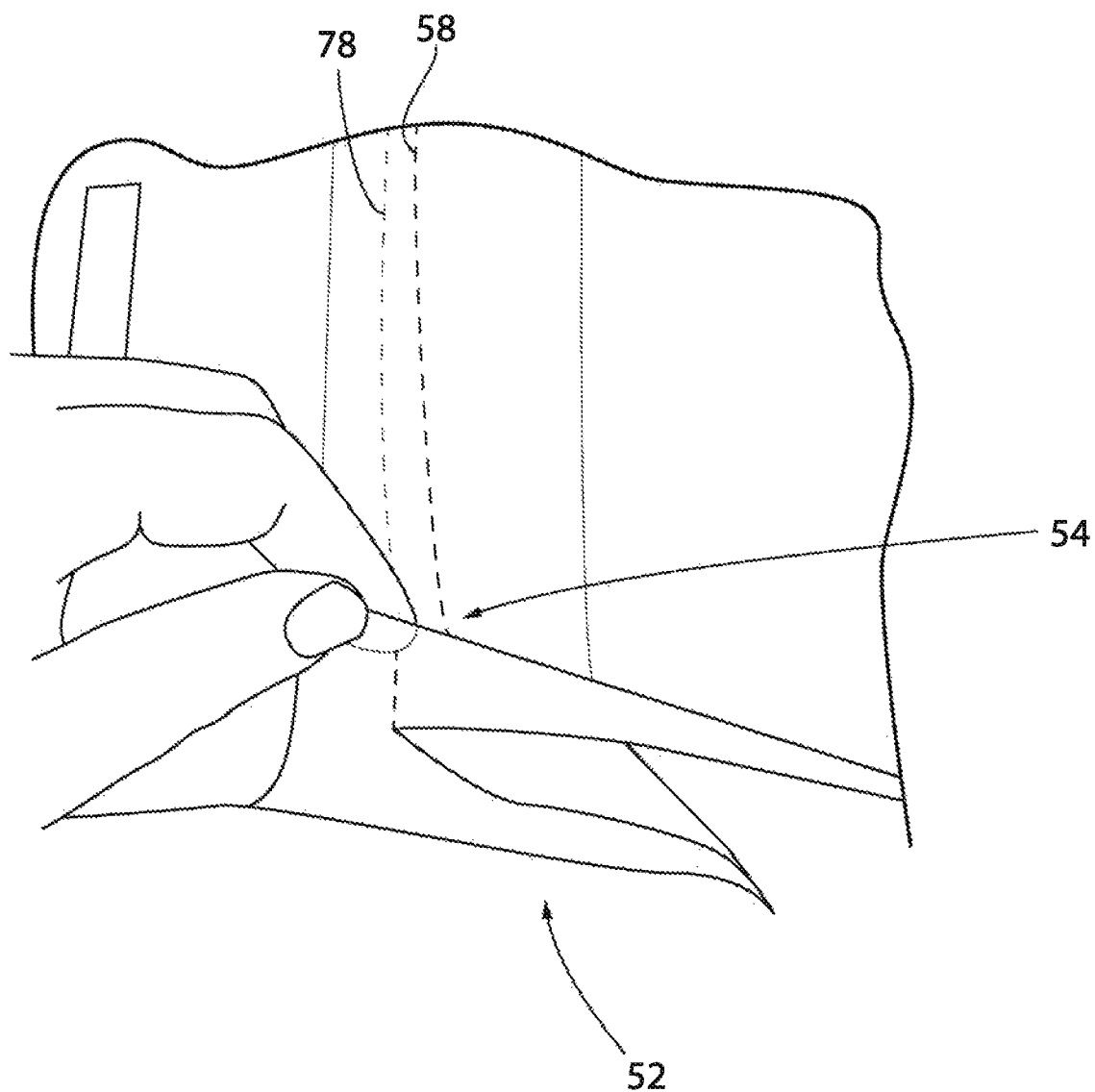
FIG. 12 illustrates another detailed perspective view of the z-fold the draping system of FIGS. 4-10.
Figure 13:
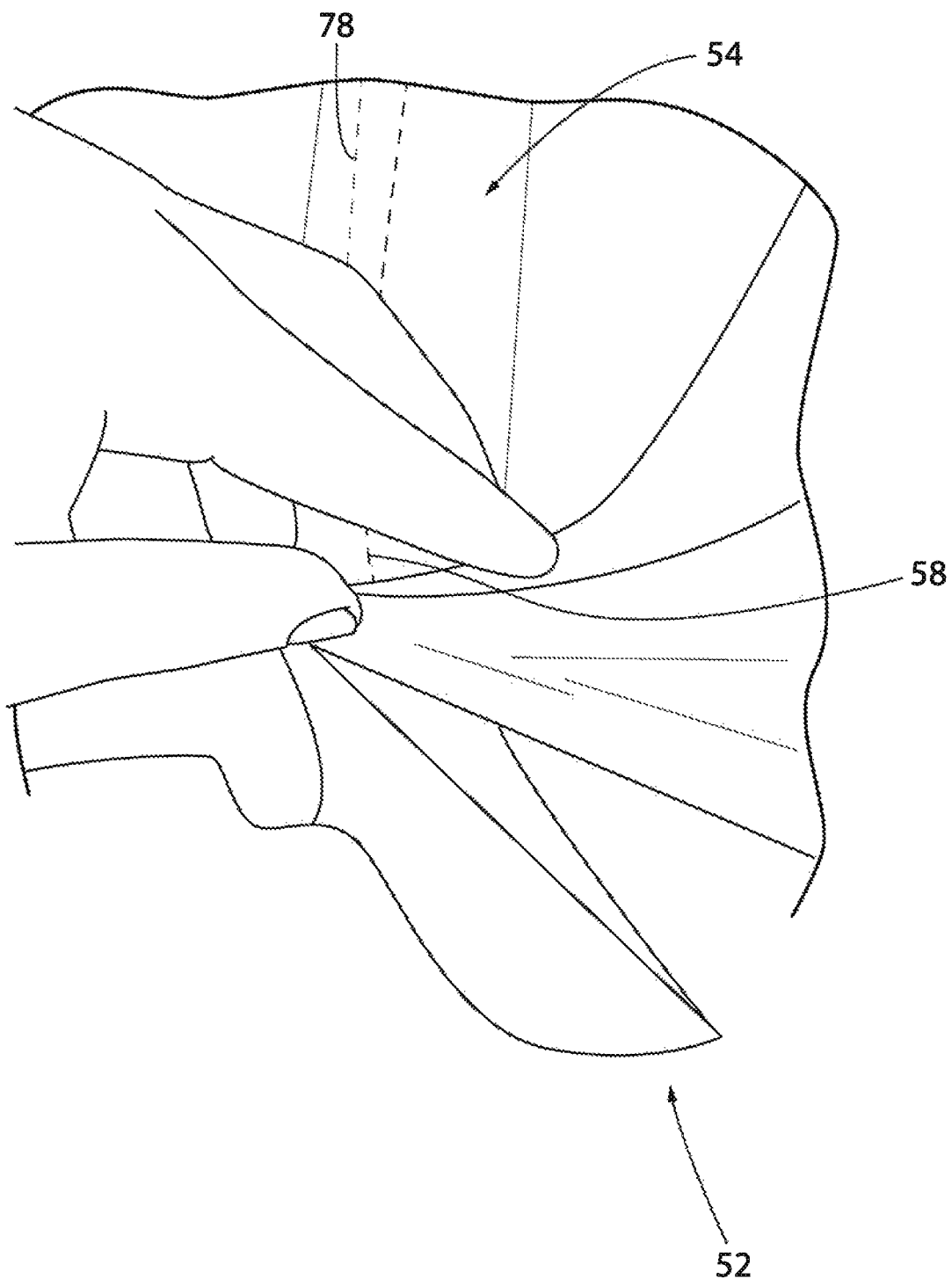
FIG. 13 illustrates a detailed perspective view of the z-fold the draping system of FIGS. 4-10 as the lock device is disengaged.
Figure 14:
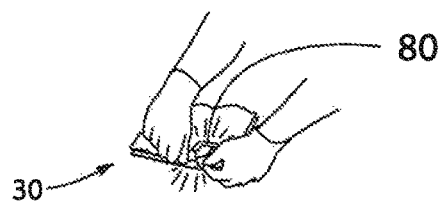
FIG. 14 illustrates a perspective view of the draping system as a directional label is broken.
Figure 15:
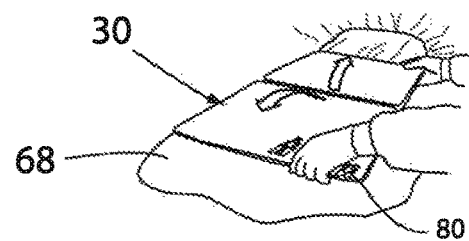
FIG. 15 illustrates a perspective view of the draping system of FIG. 14 as it is initially unfolded.
Figure 16:
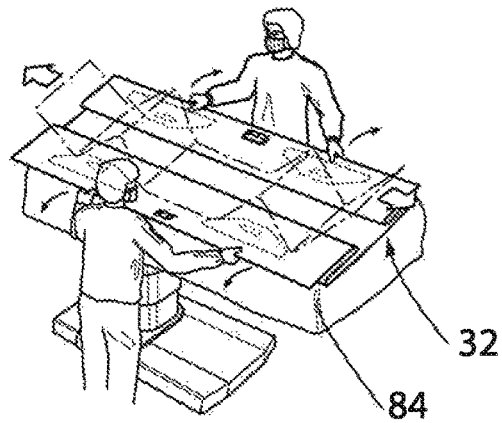
FIG. 16 illustrates a perspective view of the draping system as it is further unfolded by two employees.
Figure 17:
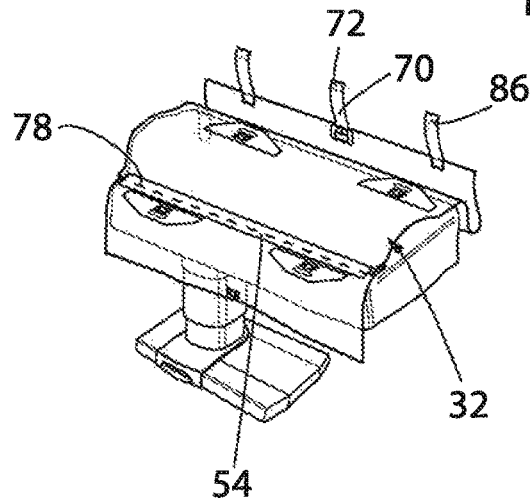
FIG. 17 illustrates a perspective view of the draping system as it is wrapped around the sterile surface.
Figure 18:
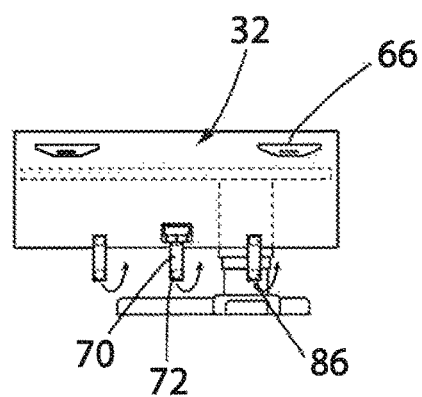
FIG. 18 illustrates a side elevation view of the draping system as it is wrapped around the sterile surface.
Figure 19:
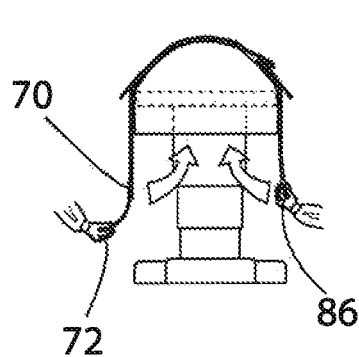
FIG. 19 illustrates an end elevation view of the draping system as the plurality of straps are wrapped around the sterile surface.
Figure 20:
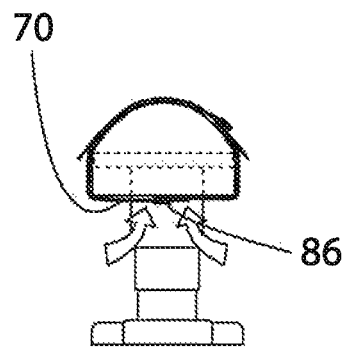
FIG. 20 illustrates an end elevation view of the draping system once the plurality of straps is secured to the drape.

While the draping system 30 is being folded, directional labels 80 may be installed to the sheet. These directional labels 80 serve to both secure adjacent portions of the draping system 30 to one another, and also to provide instruction to a user as to the way that drape 32 should be unfolded. For instance, the labels 80a shown in FIGS. 4 and 5 help to inform a user as to which side should be placed upwardly. Additionally, the labels 80b shown in FIGS. 5-7 show the direction in which the labels 80b should be broken. Further still, the labels 80c shown in FIGS. 8-10 provide arrows showing the direction in which the handles should be pulled. Also, handles 66 can be installed to the sheet 76 or formed with the sheet 76, which allow the draping system 30 to more easily be used.

A method of using the draping system 30 helps to maintain sterile conditions about an operating room during a medical procedure. Initially, the draping system 30 is removed from a sterile package and placed onto a sterile surface 68. Next, the draping system 30 is unfolded, as shown in FIGS. 4-8 and 14-16. Directional labels 80 may be included on the draping system 30 that help to instruct a user or users how to unfold and use the draping system 30.

Figure 21:
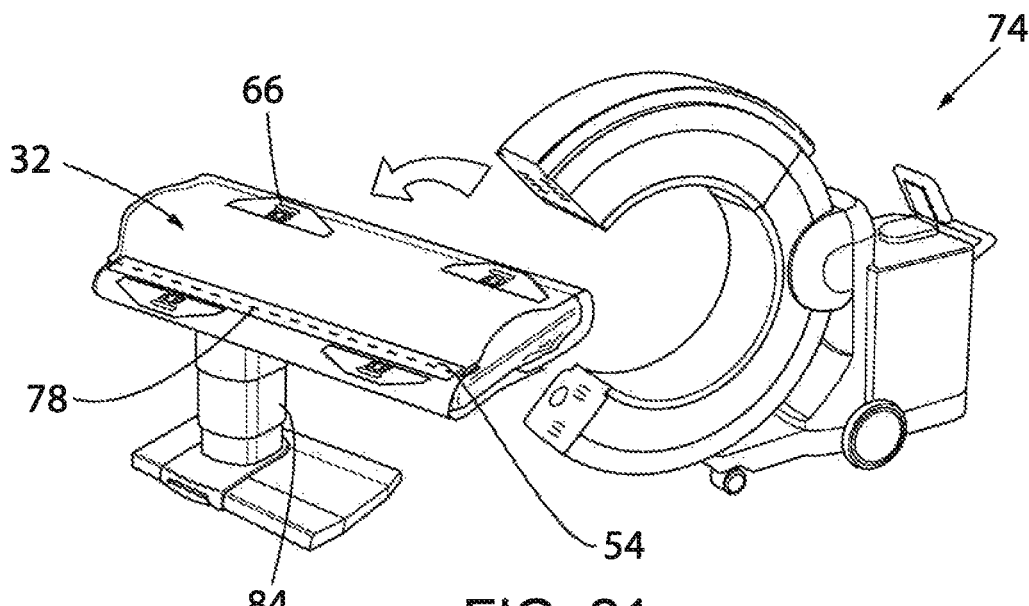
FIG. 21 illustrates a perspective view of a piece of medical equipment that is moved adjacent to the sterile surface.
Figure 22:
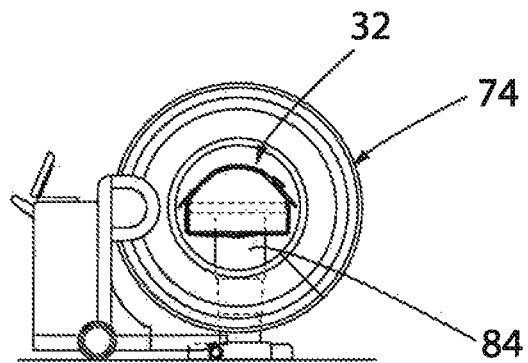
FIG. 22 illustrates a perspective view of the piece of medical equipment that is further moved adjacent to the sterile surface.

To fully install the drape 32 about the patient 82 and the operating table 84, the straps 70 are wrapped around the patient 82 and the operating table 84, and secured to either one another, the drape 32 itself, or the operating table 84 as shown in FIGS. 17-20. By securing the drape 32 beneath the table 84 using the straps 70, the system 30 allows various medical equipment 74 to be moved in close relation to the table 84 without compromising sterility, as shown in FIGS. 21 and 22.

Figure 23:
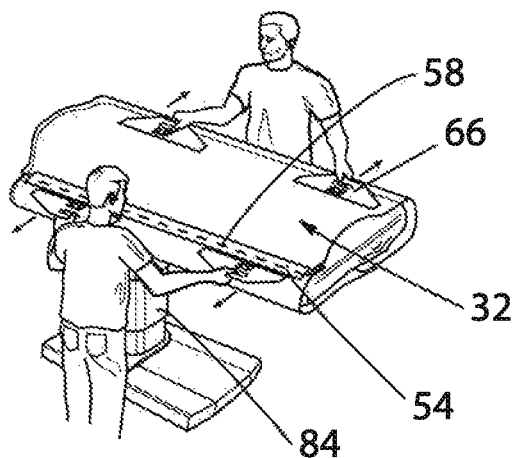
FIG. 23 illustrates a perspective view of the draping system as the draping system is pulled in two opposite directions.
Figure 24:
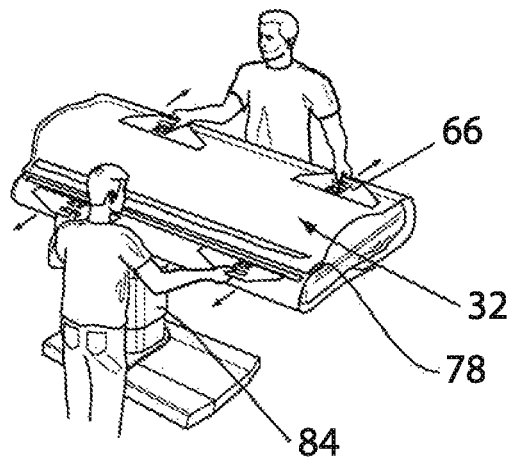
FIG. 24 illustrates a perspective view of the draping system as the lock device is disengaged.
Figure 25:
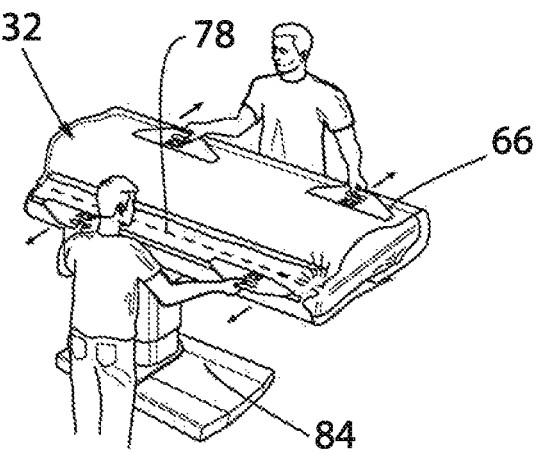
FIG. 25 illustrates a perspective view of the draping system as the drape is separated about a perforation.
Figure 26:
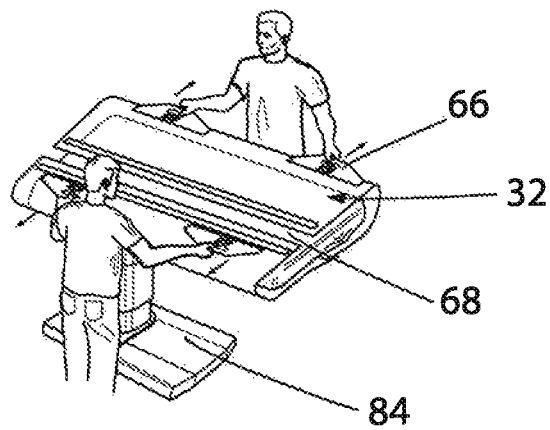
FIG. 26 illustrates a perspective view of the draping system as the selectively separable portions separate from one another.
Figure 27:
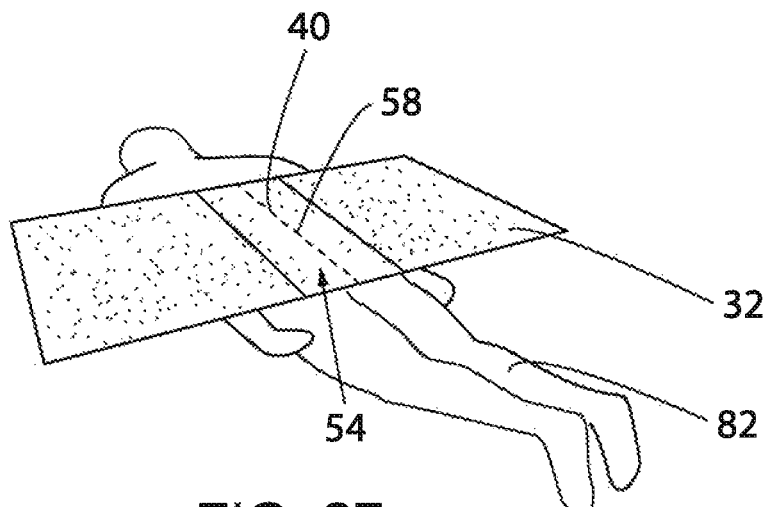
FIG. 27 illustrates a simplified perspective view of a patient located beneath the drape system.
Figure 28:
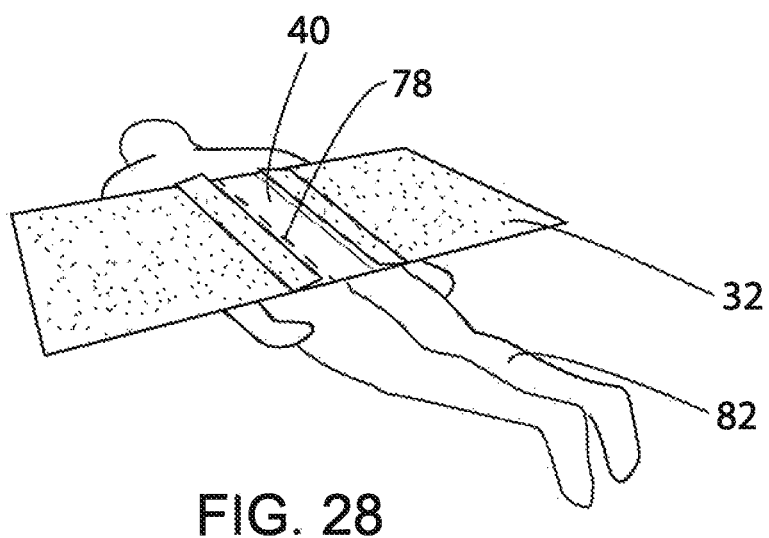
FIG. 28 illustrates a simplified perspective view of the draping system of FIG. 27 as the lock device is disengaged.
Figure 29:
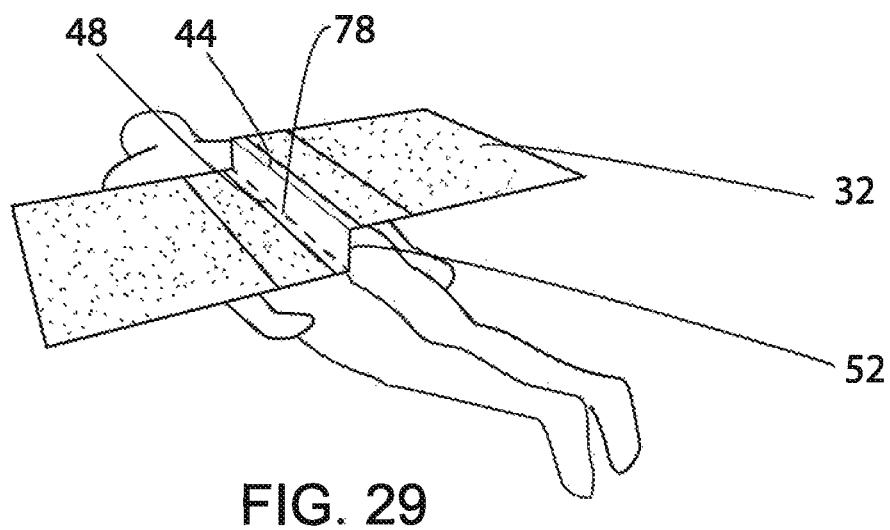
FIG. 29 illustrates a simplified perspective view of the patient located beneath the drape system after the lock device has been disengaged and while the peripheral edges are moved from one another of FIGS. 27 and 28.
Figure 30:
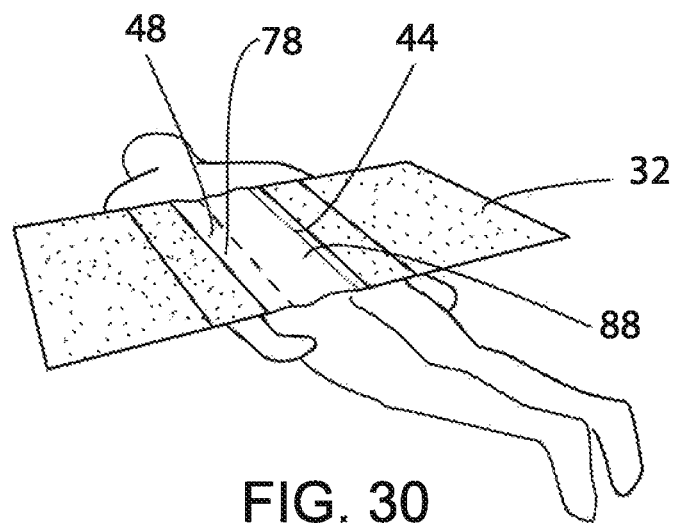
FIG. 30 illustrates a simplified perspective view of the patient located beneath the drape system once the drape system has been unfolded of FIGS. 27-29.
Figure 31:
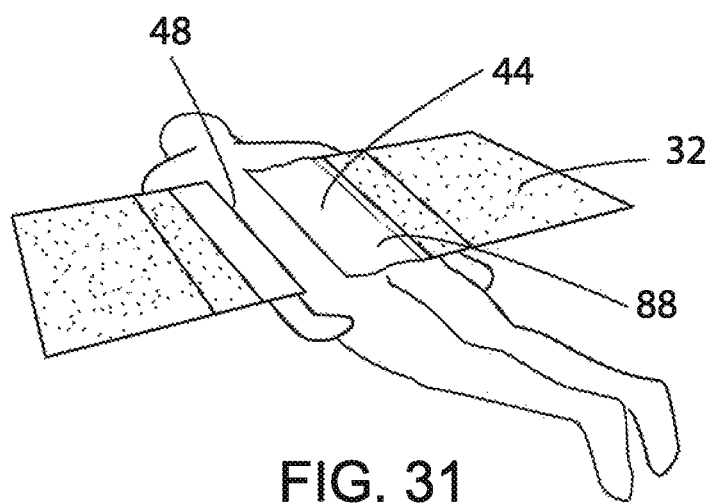
FIG. 31 illustrates a simplified perspective view of the patient once the drape system of FIGS. 27-30 has been disengaged.

See FIGS. 23-26 for views of the full system 30 in use and 27-31 for schematic views of the drape 32 in use, including the disengagement of the lock device 54 and separation of the drape 32 about perforation 78. Once fully unfolded, the lock device 54 may be disengaged as shown in FIGS. 23 and 24. To do so, opposite ends of the drape 32 are pulled away from one another. Once the lock device 54 is disengaged, further pulling results in unfolding of the z-shaped fold 52 as shown in FIGS. 29 and 30. As this is done, a sterile zone 88 is exposed that is located within the z-shaped fold 52. Further pulling still results in breaking of the drape 32 about the perforation 78, with either edge 44, 48 of the perforation 78 remaining sterile. See FIGS. 26 and 31. While this happens, sterility is maintained beneath the drape 32. Additionally, the handles 66 can be pulled in opposite directions in order to disengage the lock device 54, unfold the z-shaped fold 52, and break the drape 32 about the perforation 78. As a result, the system 30 allows the drape 32 to be easily and sterilely removed. More specifically, the drape system 30 allows both of the first peripheral edge 44 and the overlapping second peripheral edge 48 to remain sterile during the separation process.

There are virtually innumerable uses for the present invention, all of which need not be detailed here. For instance, the drape system 30 could be used in any setting where sterility concerns exist. Furthermore, the drape system 30 could be used in other contexts to shelter an environment beneath the drape system 30. All the disclosed embodiments can be practiced without undue experimentation.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept.

Similarly, any material capable of maintaining sterility could be used to create the draping system. For instance, as shown the drape is made of a sterile, substantially transparent plastic material. However, the individual components need not be fabricated from the disclosed materials, but could be fabricated from virtually any suitable materials.

Moreover, the individual components need not be formed in the disclosed shapes, or assembled in the disclosed configuration, but could be provided in virtually any shape, and assembled in virtually any configuration. Further, although the drape and the lock device are described herein as being separate modules that are later combined, it will be manifest that they may be made simultaneously using a single piece of material. Furthermore, all the disclosed features of each disclosed embodiment can be combined with, or substituted for, the disclosed features of every other disclosed embodiment except where such features are mutually exclusive.

It is intended that the appended claims cover all such additions, modifications and rearrangements. Expedient embodiments of the present invention are differentiated by the appended claims.

The invention claimed is:

1. A method for manufacturing a draping system, comprising:
    manufacturing a sheet having a predetermined length, a predetermined width, and first and second peripheral edges;
    forming a first perforation in the sheet at a midpoint of the predetermined width along the entire predetermined length;
    folding the sheet into a folded configuration such that the first peripheral edge overlaps the second peripheral edge to form a z-shaped fold, the first perforation is located between and extends substantially parallel to the first and second peripheral edges, and a portion of the sheet covers the first perforation; and
    securing a lock device to the sheet such that the sheet remains in the folded configuration until the lock device is disengaged, the lock device comprising a second perforation extending therethrough.

2. The method of claim 1, wherein the lock device comprises a poly seal with the second perforation extending therethrough.

3. The method of claim 2, wherein the poly seal comprises a strip of poly seal with the second perforation extending therethrough.

4. The method of claim 2, wherein the securing step comprises heat-sealing the poly seal to the sheet.

5. The method of claim 1, wherein the lock device comprises at least one piece of adhesive tape and the securing step comprises:
applying the at least one piece of adhesive tape to the sheet.

6. The method of claim 1, wherein the lock device comprises a plurality of hook and loop fasteners and the securing step comprises:
applying the plurality of hook and loop fasteners to the sheet; and
engaging complementary hook and loop fasteners to one another.

7. The method of claim 1, wherein, in the folding step, the first peripheral edge overlaps the second peripheral edge by about three inches.

8. The method of claim 1, further comprising installing directional labels onto the sheet.

9. The method of claim 8, wherein the directional labels secure adjacent portions of the sheet to one another.

10. The method of claim 8, wherein the directional labels are breakable.

11. The method of claim 1, further comprising attaching a plurality of handles to the sheet.

12. The method of claim 11, wherein the handles are configured to allow the lock device to be disengaged and the z-shaped fold to be unfolded.

13. The method of claim 1, wherein the first perforation is offset from the second peripheral edge.

14. The method of claim 1, wherein the second perforation is configured to allow the lock device to be disengaged and the first perforation is configured to break to allow the sheet to be separated into two opposing halves once the z-shaped fold is unfolded.

15. The method of claim 1, wherein the first perforation is located at the second peripheral edge.

* * * * *